United States Patent [19]

Maravetz

[11] Patent Number: 5,262,382
[45] Date of Patent: Nov. 16, 1993

[54] HERBICIDAL 1-PYRIDYLPYRAZOLE COMPOUNDS

[75] Inventor: Lester L. Maravetz, Westfield, N.J.

[73] Assignee: FMC Corporation, Philadelphia, Pa.

[21] Appl. No.: 953,407

[22] Filed: Sep. 4, 1992

Related U.S. Application Data

[62] Division of Ser. No. 770,697, Oct. 3, 1991, Pat. No. 5,167,691.

[51] Int. Cl.$^5$ .................... C07D 213/02; A01N 43/56
[52] U.S. Cl. ...................................... 504/130; 546/278
[58] Field of Search ................. 546/276, 278; 71/92; 504/130

[56] References Cited

U.S. PATENT DOCUMENTS

| | | | |
|---|---|---|---|
| 4,614,533 | 9/1986 | Schnaller et al. | 71/92 |
| 4,772,210 | 9/1988 | Stetter et al. | 71/92 |
| 4,772,312 | 9/1988 | Schallner et al. | 71/92 |
| 4,774,254 | 9/1988 | Stetter et al. | 514/404 |
| 4,812,165 | 3/1989 | Schallner et al. | 71/92 |

FOREIGN PATENT DOCUMENTS 2136427  9/1984  United Kingdom .................. 71/92

*Primary Examiner*—C. Warren Ivy
*Assistant Examiner*—Zinna N. Davis
*Attorney, Agent, or Firm*—H. Robinson Ertelt; Robert M. Kennedy; Robert L. Andersen

[57] ABSTRACT

This application discloses herbicidal 1-arylpyrazoles, compositions containing them, methods of preparing them, and methods for controlling undesired plant growth by preemergent or postemergent application of the herbicidal compositions to the locus where control is desired. The herbicidal compounds have the following generic structure:

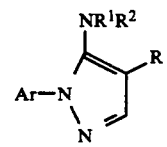

in which Ar is

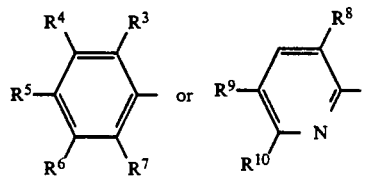

R is chlorine, cyano, or nitro; $R^1$ is a group —C(O)C$R^{11}R^{12}$—O—$R^{13}$ in which $R^{11}$ and $R^{12}$ are independently hydrogen or alkyl; $R^{13}$ is hydrogen, alkylcarbonyl, phenylcarbonyl, phenylmethyl, or alkylaminosulfonyl; $R^2$ is hydrogen, alkyl, alkylcarbonyl, alkoxycarbonyl, or a group —C(O)C$R^{11}R^{12}$—O—$R^{13}$; $R^3$, $R^4$, $R^6$, $R^7$ are independently hydrogen or halogen; $R^5$ is halogen or haloalkyl; $R^8$ is halogen; $R^9$ is haloalkyl; $R^{10}$ is hydrogen, halogen, or a group —N$R^{14}R^{15}$ in which $R^{14}$ is hydrogen or alkyl; $R^{15}$ is alkyl, alkynyl, or a group —CH$R^{16}$—Ar$^1$ in which $R^{16}$ is hydrogen or alkyl; and Ar$^1$ is tetrahydrofuran-2-yl; furan-2-yl, thien-2-yl, phenyl, or phenyl substituted with halogen or alkoxy. When $R^{10}$ is a group —N$R^{14}R^{15}$, in addition to the substituents listed above, $R^1$ may be alkylcarbonyl, haloalkylcarbonyl, or cycloalkylcarbonyl; and $R^2$ may be hydrogen, alkylcarbonyl, or cycloalkylcarbonyl.

7 Claims, No Drawings

HERBICIDAL 1-PYRIDYLPYRAZOLE COMPOUNDS

This application is a division of application Ser. No. 770,697, filed Oct. 3, 1991, now U.S. Pat. No. 5,167,691.

This invention pertains to novel herbicidal 1-(substituted-aryl)-5-substituted-carbonylamino-4-substituted-pyrazoles for weed control in agriculture, horticulture, and other fields in which it is desired to control unwanted plant growth, such as grassy or broadleaf plant species. In particular it pertains to 1-(substituted-phenyl)- and 1-(substituted-pyridin-2-yl)-5-substituted-carbonylamino-4-(nitro/cyano/chloro)pyrazoles as pre- and postemergence herbicides.

A variety of herbicidal 1-arylpyrazoles have previously been described. For example, U.S. Pat. No. 4,812,165 describes compounds of the formula

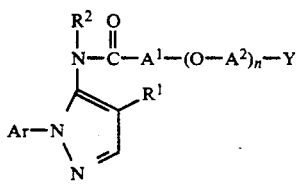

wherein

Ar represents an optionally substituted phenyl or pyridyl (including 2,3,5,6-tetrafluoro-4-trifluoromethlilphenyl and 3-chloro-5-trifluorourethylpyridin-2-yl) ;

$R^1$ represents hydrogen or nitro;

$R^2$ represents hydrogen, alkyl or a radical —C(O)—$A^1$—(O—$A^2$)$_n$—Y;

$A^1$ and $A^2$ independently represent a divalent alkylene radical;

Y includes hydroxyl, substituted alkoxy, or a radical —O—C(O)—$R^3$ $R^3$ includes hydrogen, alkyl, alkoxy, amino, and substituted amino; and n is 1, 2, 3, or 4.

U.S. Pat. No. 4,614,533 describes compounds of the formula

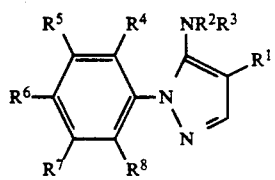

wherein $R^1$ includes hydrogen, nitro, halogen;

$R^2$ is hydrogen or a radical —C(O)$R^{12}$ $R^3$, independently of $R^2$. is hydrogen, —C(O)$R^{12}$, or alkyl;

$R^4$-$R^8$ include hydrogen, halogen, alkyl, and haloalkyl;

$R^{12}$ includes alkoxyalkyl and alkylthioalkyl.

U.S. Pat. No. 4,772,312 describes compounds of the formula

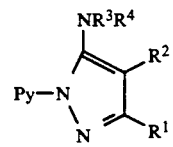

wherein $R^1$ is hydrogen or alkyl;

$R^2$ includes hydrogen, halogen, nitro;

$R^3$ is hydrogen or a radical —C(O)$R^6$;

$R^4$ is a hydrogen, alkyl, or a radical —C(O)$R^6$R $R^6$ includes alkoxyalkyl and alkylthioalkyl;

Py is a 2-, 3-, or 4-pyridyl group which is substituted with halogen, cyano, nitro, alkyl, alkoxy, alkoxycarbonyl, haloalkyl, haloalkoxy, or a group —S(O)$_m$$R^9$ where m is 0, 1, or 2; and $R^9$ is alkyl, amino, substituted amino, or haloalkyl.

U.S. Pat. No. 4,787,930 describes compounds of the formula

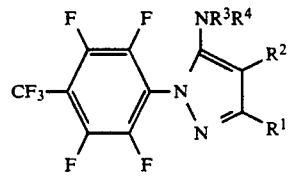

in which $R^1$ includes hydrogen;

$R^2$ includes hydrogen, nitro, or halogen;

$R^3$ is hydrogen, or represents a radical —C(X)$R^6$ or —S(O)n$R^7$ and $R^4$ is hydrogen, or alkyl, or represents a radical —C(X)—$R^6$ or —S(O)n—$R^7$, or, in the case where $R^3$ represents a —SO2—$R^7$ radical or a —C(O)—C$_m$F$_{2m+1}$ radical, also represents an inorganic or organic cation bonded in salt form;

wherein $R^6$ represents hydrogen, alkyl, alkenyl, alkynyl, halogenoalkyl, alkoxyalkyl, alkylthioalkyl, alkylsulfonylalkyl or alkylsulfinylalkyl, or represents optionally substituted cycloalkyl, optionally substituted aryl, or represents alkoxy or alkylthio, optionally substituted aryloxy, optionally substituted arylthio, alkylamino, dialkylamino or optionally substituted arylamino, X represents oxygen or sulfur;

n represents the number 0, 1 or 2;

m represents the number 1, 2 or 3; and $R^7$ represents alkyl, halogenoalkyl, or optionally substituted aryl;

but wherein, in the case where $R^1$ and $R^3$ represent hydrogen and $R^2$ represents nitro, $R^4$ does not simultaneously represent a propionyl radical.

U.S. Pat. No. 4,770,693 describes compounds of the formula

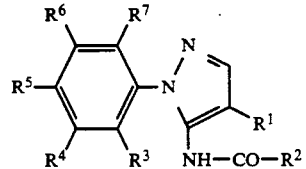

in which

R[1] represents cyano, alkoxycarbonyl, alkenyloxycarbonyl, alkynyloxycarbonyl, aminocarbonyl, alkylaminocarbonyl, alkenylaminocarbonyl or alkynylaminocarbonyl;

R[2] represents hydrogen, alkyl, alkenyl, alkynyl, optionally substituted cycloalkyl, alkoxyalkyl, alkylthioalkyl, halogenoalkyl or optionally substituted aryl; and R[3], R[4], R[5], R[6] and R[7], which are identical or different, represent hydrogen, halogen, cyano, nitro, alkyl, alkoxy, alkylsulfonyl, alkoxycarbonyl or radical —(X)$_n$—R[8] wherein X represents oxygen, sulfur, sulfinyl or sulfonyl, n represents 0 or 1; and R[8] represents halogenoalkyl, provided that at least one of the radicals R[3], R[4], R[5], R[6], and R[7] represents a radical —(X)$_n$—R[8], but R[1] does not represent cyano if R[5] represents trifluoromethyl.

German patent application DE 3,520,327-A discloses the following 5-amino-4-cyano-i-pyridylpyrazoles as herbicides:

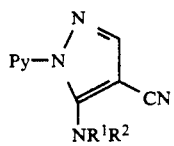

wherein

R[1] and R[2] are hydrogen, optionally substituted alkyl, alkenyl, alkynyl or cycloalkyl, or CXR[3];

X is O or S;

R[3] is hydrogen, alkyl, alkoxy, alkoxyalkyl, alkylthio, alkylthioalkyl, haloalkyl, alkenyl, alkynyl, optionally substituted cycloalkyl, aryl, aryloxy, arylthio or arylamino, or mono or dialkylamino; and py is substituted pyridyl, but not 5-nitro-2- pyridyl or 3-chloro-5-trifluoromethyl-2-pyridyl.

Other patents and published patent applications which further define the state of the art include U.S. Pat. Nos. 4,459,150, 4,746,354, 4,772,310, 4,774,254, and 4,936,892, European Patent 303,143A2, and Great Britain Patent Applications 2,123,420A and 2,136,427A.

An article by M. Dooley, et al., (Aust. J. Chem., 1989, 42, 747–50) describes the preparation of 1-(substituted-phenyl)-5-amino-4-cyanopyrazoles, intermediates in the present case, in a one-pot reaction between substituted hydrazines, malononitrile, and triethyl orthoformate. This process is similar to that described in Step A of Example 1 of this application.

It has now been found that 1-(substituted-aryl)-5-substituted-carbonylamino-4-substituted-pyrazoles are highly active pre- and postemergence herbicidal compounds. The novel compounds of this invention differ from the compounds of the prior art especially in the nature of the substituent on the 5-amino group of the pyrazole ring.

DETAILED DESCRIPTION OF THE INVENTION

The novel 1-(substituted-aryl)-5-substituted-carbonylamino-4-substituted-pyrazoles of the present invention are described by the following generic structure:

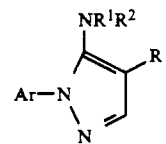

wherein Ar is selected from:

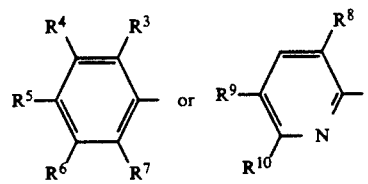

R is selected from chlorine, cyano, or nitro;

R[1] is a group —C(O)CR[11]R[12]—O—R[13] in which R[11] and R[12] are independently hydrogen or alkyl; R[13] is selected from hydrogen, alkylcarbonyl, phenylcarbonyl, phenylmethyl, or alkylaminosulfonyl;

R[2] is selected from hydrogen, alkyl, alkylcarbonyl, alkoxycarbonyl, or a group —C(O)CR[11]R[12]—O—R[13];

R[3], R[4], R[6], R[7] are independently selected from hydrogen or halogen;

R[5] is selected from halogen or haloalkyl;

R[8] is halogen;

R[9] is haloalkyl;

R[10] is hydrogen, halogen, or a group —NR[14]R[15] in which R[14] is selected from hydrogen or alkyl; R[15] is alkyl, alkynyl, or a group —CHR[16]—Ar[1] in which R[16] is selected from hydrogen or alkyl; and Ar[1] is selected from tetrahydrofuran-2-yl; furan-2-yl, thien-2-yl, and phenyl or phenyl substituted with halogen or alkoxy, and when R[10] is a group —NR[14]R[15], in addition to the substituents listed above, R[1] may be alkylcarbonyl, haloalkylcarbonyl, or cycloalkylcarbonyl; and R[2] may be hydrogen, alkylcarbonyl, or cycloalkylcarbonyl.

Preferred are those compounds in which each alkyl and alkoxy contains 1 to 4 carbon atoms, each cycloalkyl contains 3–6 carbon atoms, and each alkynyl contains 3–4 carbon atoms.

The compounds of this invention were prepared by one of the following routes:

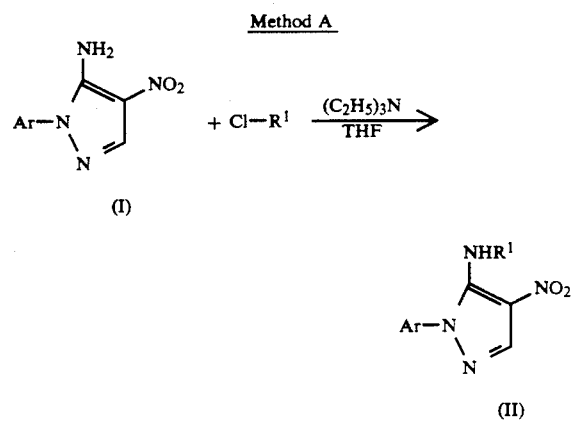

The process for the production of compounds of formula (I) has been disclosed in U.S. Pat. No. 4,787,930 and in U.S. Pat. No. 4,772,312. The reaction of (I) with an appropriately substituted acetyl chloride (e.g., Cl—R$^1$=acetoxyacetyl chloride) and triethylamine in tetrahydrofuran (THF) yielded a 1-(substituted-aryl)-5-(substituted-methylcarbonyl)amino-4-nitropyrazole (II).

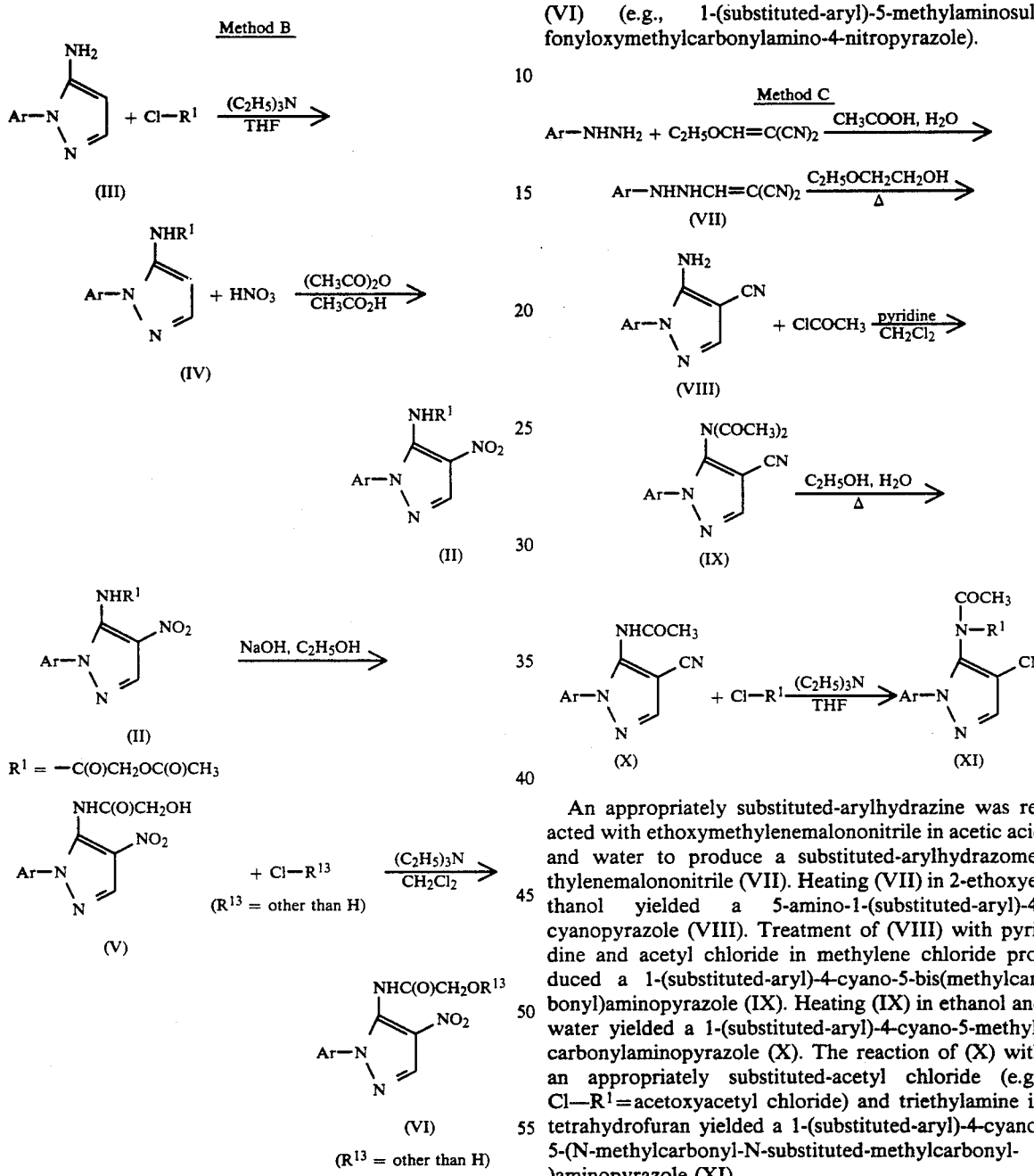

This alternative method for producing compounds of formula (II) begins with the reaction of a 5-amino-1-(substituted-aryl)pyrazole of formula (III) with an appropriately substituted-acetyl chloride and triethylamine in tetrahydrofuran to produce a 1-(substituted-aryl)-5-(substituted-methylcarbonyl)aminopyrazole (IV). Subsequent nitration of (IV) with nitric acid in acetic anhydride and acetic acid produced a 1-(substituted-aryl)-5-(substituted-methylcarbonyl)amino-4-nitropyrazole of formula (II). In cases where the R$^1$ group of (II) was methylcarbonyloxymethylcarbonyl, the compound was treated with sodium hydroxide in ethanol to yield a 1-(substituted-aryl)-5-hydroxymethylcarbonylamino-4-nitropyrazole (V). The reaction of (V) with a chloride of an R$^{13}$ group (e.g., methylazinosulfonyl chloride) yielded a 1-(substituted-aryl)—S-(substituted-oxymethylcarbonyl)amino-4-nitropyrazole (VI) (e.g., 1-(substituted-aryl)-5-methylaminosulfonyloxymethylcarbonylamino-4-nitropyrazole).

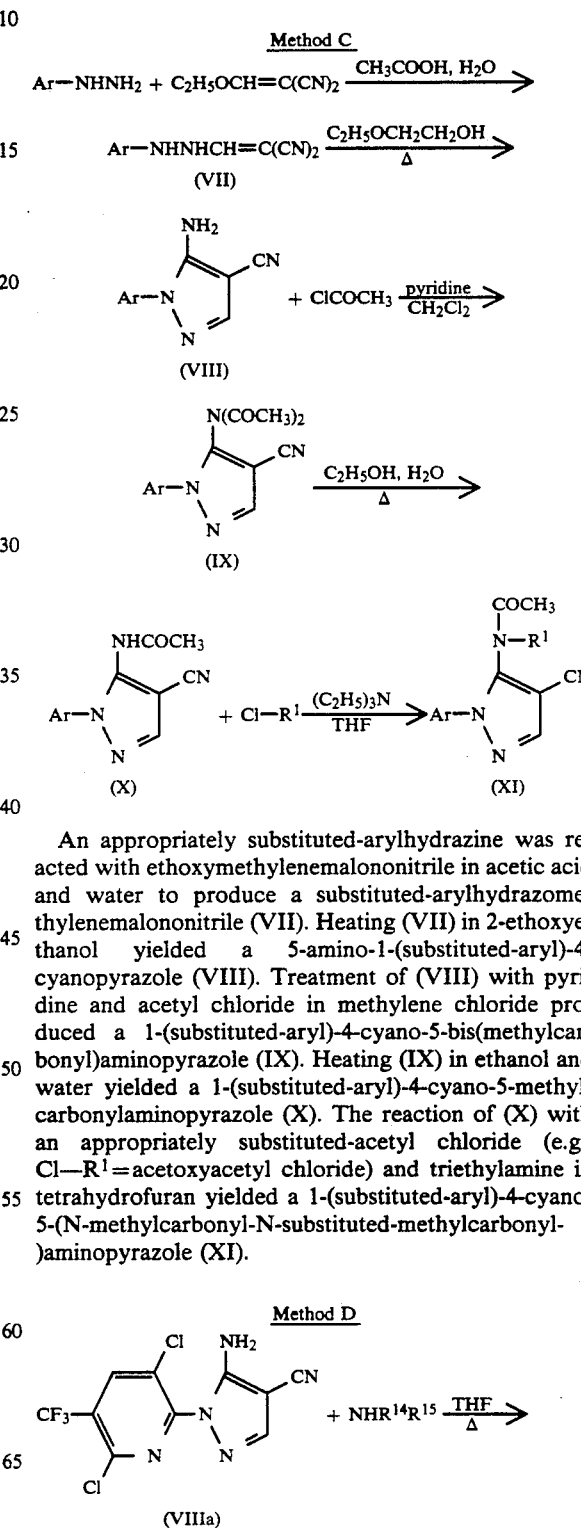

An appropriately substituted-arylhydrazine was reacted with ethoxymethylenemalononitrile in acetic acid and water to produce a substituted-arylhydrazomethylenemalononitrile (VII). Heating (VII) in 2-ethoxyethanol yielded a 5-amino-1-(substituted-aryl)-4-cyanopyrazole (VIII). Treatment of (VIII) with pyridine and acetyl chloride in methylene chloride produced a 1-(substituted-aryl)-4-cyano-5-bis(methylcarbonyl)aminopyrazole (IX). Heating (IX) in ethanol and water yielded a 1-(substituted-aryl)-4-cyano-5-methylcarbonylaminopyrazole (X). The reaction of (X) with an appropriately substituted-acetyl chloride (e.g., Cl—R$^1$=acetoxyacetyl chloride) and triethylamine in tetrahydrofuran yielded a 1-(substituted-aryl)-4-cyano-5-(N-methylcarbonyl-N-substituted-methylcarbonyl)aminopyrazole (XI).

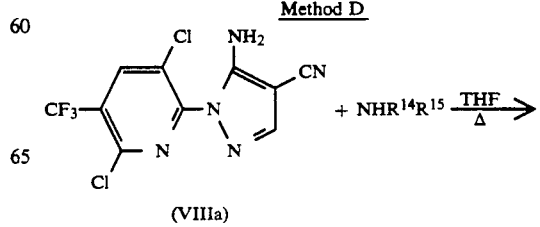

-continued

Method D

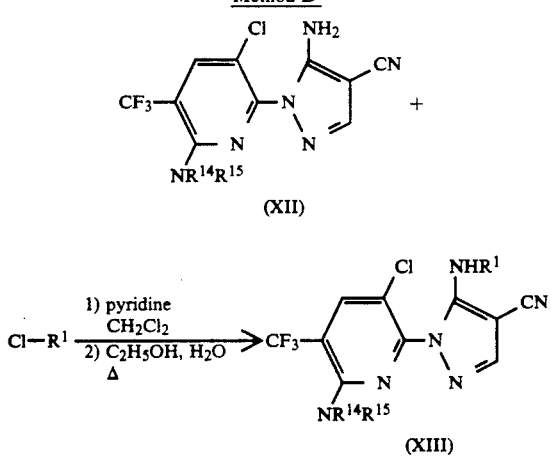

In cases where the compound of formula (VIII) was 5-amino-1-(3,6-dichloro-5-trifluoromethylpyridin-2-yl)-4-cyanopyrazole (VIIIa), an —NR$^{14}$R$^{15}$ group was added by heating this compound with an appropriately substituted amine (e.q., benzylamine) in tetrahydrofuran producing a 5-amino-1-(3-chloro-5-trifluoromethyl-6-substituted-aminopyridin-2-yl)-4-cyanopyrazole (XII). The reaction of (XII) with an appropriately substituted-acetyl chloride (e.g., Cl—R$^{1}$=propionyl chloride) yielded a 5-substituted-carbonylamino-1-(3-chloro-5-trifluoromethyl-6-substituted-aminopyridin-2-yl)-4-cyanopyrazole (XIII).

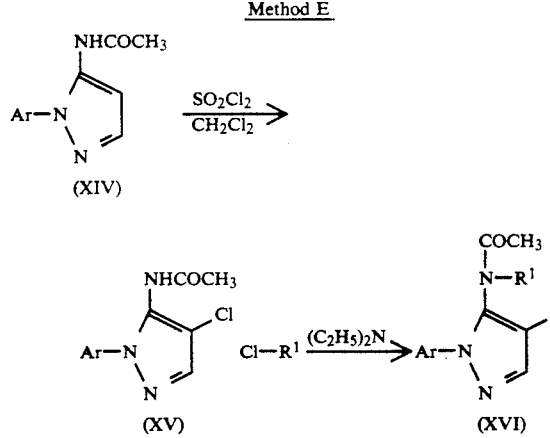

To produce a pyrazole with a chlorine in the 4-position, a compound of formula (XIV) was treated with sulfuryl chloride in methylene chloride. This process is disclosed in U.S. Pat. No. 4,787,930. Reaction of (XV) with an appropriately substituted-acetyl chloride (e.g., acetoxyacetyl chloride) and triethylamine in tetrahydrofuran yielded a 4-chloro-1-(substituted-aryl)-5-(N-methylcarbonyl-N-substituted-methylcarbanyl-)aminopyrazole (XVI).

Each of these methods of preparation is exemplified below.

EXAMPLE 1

Method A 1-(2,3,5,6-Tetrafluoro-4-Trifluoromethylphenyl)-5-Methylcarbonyloxymethylcarbonylamino-4-Nitropyrazole (Compound 14)

Step A Ethyl 5-amino-1-(2,3,5,6-tetrafluoro-4-trifluoromethyl-phenyl)pyrazole-4-ylcarboxylate To a stirred solution of 15.7 grams (0.634 mole) of 2,3,5,6-tetrafluoro-4-trifluoromethylphenylhydrazine in 40 mL of anhydrous ethanol was added 10.7 grams (0.634 mole) of ethyl 2-cyano-3-ethoxyacrylate. The reaction mixture was heated at reflux for 21 hours, then cooled, and the solvent was removed by distillation under reduced pressure, leaving a residue. This residue was suspended in 80 mL of a 50:50 mixture of diethyl ether/n-pentane. A solid formed and was removed by filtration to yield 20.4 grams of ethyl 5-amino-1-(2,3,5,6-tetrafluoro-4-trifluoramethylphenyl)pyrazol-4-ylcarboxylate, m.p. 166°–1680° C. The nmr spectrum was consistent with the proposed structure.

Step B

5-Amino-1-(2,3,5,6-tetrafluoro-4-trifluoromethyl-phenyl)pyrazole

A stirred mixture of 18.6 grams (0.500 mole) of ethyl 5-amino-1-(2,3,5,6-tetrafluoro-4-trifluoromethyl-phenyl)pyrazole-4-ylcarboxylate, 23 mL of water, and 23 mL of sulfuric acid was heated at 130° C. for six hours. After the reaction mixture was cooled, 75 mL of crushed ice was added. A solid had formed and was collected by filtration; the filtrate was saved. This solid was washed with water and diethyl ether, allowed to dry, and set aside for further purification. To the filtrate was added an aqueous sodium hydroxide solution until a pH of 9.0 was obtained. A solid formed and was collected by filtration. This solid was washed with water and dried to yield 3.8 grams of 5-amino-1-(2,3,5,6-tetrafluoro-4-trifluoromethylphenyl)pyrazole, m.p. 102.5°–104.5° C. The nmr spectrum was consistent with the proposed structure.

The solid that had been set aside was stirred in 50 mL of water, and the pH of the mixture was adjusted to 9.0 with an aqueous sodium hydroxide solution. The aqueous mixture was stirred for ten minutes and then filtered. The filter cake was washed with water and dried to yield an additional 4.15 grams of product, m.p. 102.5°–104.0° C. The nmr spectrum was consistent with the proposed structure.

Step C 1-(2,3,5,6-Tetrafluoro-4-trifluoromethylphenyl)-5-methylcarbonylaminopyrazole A mixture of 7.48 grams (0.0250 mole) of 5-amino-1-(2,3,5,6-tetrafluoro-4-trifluoromethylphenyl)pyrazole, 21.0 mL of glacial acetic acid, and 3.1 mL of acetic anhydride was stirred at room temperature for approximately 18 hours. The reaction mixture was poured into 100 mL of ice-water, forming a white precipitate. This solid was collected by filtration and washed in succession with dilute acetic acid and water. The washed solid was dried to yield 8.1 grams of 1-(2,3,5,6-tetrafluoro-4-trifluoromethylphenyl)-5-methylcarbonylaminopyrazole, m.p. 103°–105° C. The nmr spectrum was consistent with the proposed structure.

Step D
1-(2,3,5,6-Tetrafluoro-4-trifluoramethylphenyl)-5-methylcarbonylamino-4-nitropyrazole A stirred solution of 7.86 grams (P.0230 mole) of 1-(2,3,5,6-tetrafluoro-4-trifluoromethylphenyl)-5-methylcarbonylaminopyrazole in 20 mL of glacial acetic acid was cooled in an ice-water bath. Acetic anhydride (2.9 mL, 0.031 mole) was added dropwise, and the mixture was stirred briefly. Concentrated nitric acid (1.05 mL, 0.0245 mole) was added dropwise, and the reaction mixture was allowed to warm to room temperature and was stirred for four hours. The mixture was poured into 60 mL of ice-water and stirred, forming a granular yellow solid. This solid was collected by filtration and washed with water. The solid was purified by recrystallization from ethanol and water to yield 5.63 grams of 1-(2,3,5,6-tetrafluoro-4-trifluoromethyl phenyl)-5-methylcarbonylamino-4-nitropyrazole, m.p. 136.5°–138.5° C. The nmr spectrum was consistent with the proposed structure.

Step E
5-Amino-1-(2,3,5,6-tetrafluoro-4-trifluoromethylphenyl)-4-nitropyrazole To a stirred solution of 5.63 grams (0.0146 mole) of 1-(2,3,5,6-tetrafluoro-4-trifluoromethylphenyl)-5-methylcarbonylamino-4-nitropyrazole in 21 mL of ethanol was added 12.0 mL (0.0144 mole) of concentrated hydrochloric acid. The reaction mixture was heated at reflux for approximately 24 hours, then cooled, and the ethanol was removed by distillation under reduced pressure, leaving an acidic residue. Water (10.5 mi) was added to this residue, and the mixture was made basic (pH 9.0) by the slow addition of an aqueous sodium hydroxide solution. The yellow solid that formed was collected by filtration. This solid was dried to yield 4.9 grams of 5-amino-1-(2,3,5,6-tetrafluoro-4-trifluoramethylphenyl)-4-nitropyrazole, m.p. 121.5°–123.0° C. The nmr spectrum was consistent with the proposed structure.

Step F
1-(2,3,5,6-Tetrafluoro-4-trifluoromethylphenyl)-5-methylcarbonyloxymethylcarbonylamino-4-nitropyrazole To a stirred solution of 0.68 gram (0.0020 mole) of 5-amino-1-(2,3,5,6-tetrafluoro-4-trifluoromethylphenyl)-4-nitropyrazole and 0.42 gram (0.0042 mole) of triethylamine in 20 mL of tetrahydrofuran was added dropwise a solution of 0.55 gram (0.0040 mole) of acetoxyacetyl chloride in 8 mL of tetrahydrofuran. The reaction mixture was heated at reflux for two hours. An additional 0.43 gram of acetoxyacetyl chloride and 0.22 gram of triethylamine were added, and the mixture was heated at reflux for 20 minutes. The mixture was cooled and filtered,, and the filtrate was evaporated under reduced pressure, leaving an oil. This oil was purified by column chromatography on silica gel, eluted with ethyl acetate/n-hexane (50:50) to yield 0.11 gram of 1-(2,3,5,6-tetrafluoro-4-trifluoromethylphenyl)-5-methylcarbonyloxymethylcarbonylamino-4-nitropyrazole as a waxy solid, Compound 14 of Table 1. The nmr spectrum was consistent with the proposed structure.

EXAMPLE 2
Method B
1-(2,3,5,6-Tetrafluoro-4-Trifluoromethylphenyl)-5-Methylaminosulfonyloxymethylcarbonylamino-4-NITROPYRAZOLE (Compound 21)

Step A
1-(2,3,5,6-Tetrafluora-4-trifluoromethylphenyl)-5-methylcarbonyloxymethylcarbonylaminopyrazole To a cold (0° C.), stirred solution of 7.0 grams (0.0234 mole) of 5-amino-1-(2,3,5,6-tetrafluoro-4-trifluoromethylphenyl)pyrazole (Example 1, Step B) and 2.76 grams (0.0273 mole) of triethylamine in 45 mL of tetrahydrofuran was added a solution of 3.54 grams (0.0259 mole) of acetoxyacetyl chloride in 5 mL of tetrahydrofuran. After the addition was complete, the reaction mixture was allowed to warm to room temperature. After the mixture had been stirred for 24 hours, an additional 25 mL of tetrahydrofuran and 2.66 grams (0.0263 mole) of triethylamine were added. The reaction mixture was heated at reflux temperature for two hours. While the mixture was at reflux, triethylamine (1.4 grams, 0.0139 mole) and acetoxyacetyl chloride (0.89 gram, 0.0065 mole) were added to the mixture. After an additional hour at reflux the mixture was cooled and filtered. The solvents were removed by evaporation under reduced pressure, leaving a brown solid residue. The solid residue was washed in succession with a mixture of diethyl ether and water and then fresh diethyl ether to yield 6.6 grams of a white solid. A portion of this white solid (4.65 grams) was added to 100 mL of ethanol and 50 mL of water, stirred, and heated at reflux for 1.75 hours. The mixture was cooled, and the ethanol was removed by distillation under reduced pressure. The aqueous residue was extracted with methylene chloride. The organic extract was washed with water. The organic phase was dried over anhydrous magnesium sulfate and filtered. Evaporation of the filtrate under reduced pressure yielded 3.92 grams of 1-(2,3,5,6-tetrafluora-4-trifluoromethylphenyl)-5-methylcarbonyloxymethyl-carbonylaminopyrazole as a pale yellow ail. The nmr spectrum was consistent with the proposed structure.

Step B
1-(2,3,5,6-Tetrafluoro-4-trifluoromethylphenyl)-5-methylcarbonyloxymethylcarbonylamino-4-nitropyrazole A mixture of 3.63 grams of 1-(2,3,5,6-tetrafluoro-4-trifluoromethylphenyl)-5-methylcarbonyloxymethylcarbonylaminopyrazole, 0.5 mL of concentrated nitric acid, and 1.53 grams (0.0150 mole) of acetic anhydride in 9.4 mL of glacial acetic acid was stirred at room temperature for two hours. This mixture was poured into ice-water, forming a yellow solid. This solid was collected by filtration and was dried to yield 3.50 grams of 1-(2,3,5,6-tetrafluoro-4-trifluoromethylphenyl)-5-methylcarbonyloxymethylcarbonylamino-4-nitropyrazole. The nmr spectrum was consistent with the proposed structure.

Step C
1-(2,3,5,6-Tetrafluoro-4-trifluoromethylphenyl)-5-hydroxymethylcarbonylamino-4-nitropyrazole A mixture of 1.5 grams (0.0034 mole) of 1-(2,3,5,6-tetrafluoro-4-trifluoromethylphenyl)-5-methylcarbonyloxymethylcarbonylamino-4-nitropyrazole, 2.63 mL of a 2N aqueous sodium hydroxide solution, 1.5 mL of ethanol, and 4.7 mL of water was stirred at room temperature for 15 minutes. After the pH was adjusted to 5.0 with dilute hydrochloric acid, ethanol was removed from the mixture by distillation under reduced pressure. The remaining aqueous phase was extracted with methylene chloride, and the extract was washed with water. The washed organic phase was dried over anhydrous magnesium sulfate and filtered. The filtrate was evaporated under reduced pressure to yield 0.75 gram of 1-(2,3,5,6-tetrafluoro-4-trifluoromethylphenyl)-5-hydroxymethylcarbonylamino-4-nitropyrazole as a solid (compound 19 of Table 1). The nmr spectrum was consistent with the proposed structure.

Step D
1-(2,3,5,6-Tetrafluoro-4-trifluoromethylphenyl)-5-methylaminosulfonyloxymethylcarbonylamino-4-nitropyrazole A stirred solution of 0.48 gram (0.0012 mole) of 1-(2,3,5,6-tetrafluoro-4-trifluoromethylphenyl)-5-hydroxymethylcarbonylamino-4-nitropyrazole and 0.27 gram (0.0027 mole) of triethylamine in 28.5 mL of methylene chloride was cooled in an ice-water bath. Methylaminosulfonyl chloride (0.55 gram, 0.0043 mole) was added dropwise, and the mixture was allowed to warm to room temperature and stir for four hours. The reaction mixture was filtered to remove a salt that had formed. The filtrate was extracted in succession with water, dilute hydrochloric acid, a saturated, aqueous sodium bicarbonate solution, and water. The organic phase was dried over anhydrous magnesium sulfate and filtered. The filtrate was evaporated under reduced pressure, leaving a brown oil. This oil was purified by column chromatography on silica gel, which was eluted with ethyl acetate: n-heptane (1:1) to yield an oil. This oil crystallized in methylene chloride and n-heptane to yield 0.07 gram of 1-(2,3,5,6-tetrafluoro-4-trifluoro methylphenyl)-5-methylaminosulfonyloxymethylcarbonylamino-4-nitropyrazole as an ivory-colored solid (Compound 21 of Table 1). The nmr spectrum was consistent with the proposed structure.

EXAMPLE 3

Method C
1-(3-Chloro-5-Trifluoromethlpyridin-2-yl)-4-Cyano-5-(N-Methylcarbonyl-N-Methylcarbonyloxymethylcarbonyl)aminopyrazole (Compound 26)

Step A
(3—Chloro-5-trifluoromethylpyridin-2-yl)hydrazomethylenemalononitrile To a stirred solution of 12.2 grams (0.100 mole) of ethoxymethylenemalononitrile in 80 mL of water and 160 mL of glacial acetic acid was added 21.2 grams (0.100 mole) of (3-chloro-5-trifluoromethylpyridin-2-yl)hydrazine. The reaction mixture was stirred briskly to dissolve the hydrazine, resulting in a clear, red solution. On stirring at room temperature for five hours, this solution formed a thick slurry, which was diluted with 600 mL of water and filtered. The filter cake was washed with water and dried to yield 20.0 grams of (3-chloro-5-trifluoromethylpyridin-2-yl)hydrazomethylenemalononitrile. The nmr spectrum was consistent with the proposed structure.

Step B
5-Amino-1-(3-chloro-5-trifluoromethylpyridin-2-yl)-4-cyanopyrazole

A stirred solution of 19.0 grams (0.066 mole) of (3-chloro-5-trifluoramethylpyridin-2-yl)hydrazomethylenemalononitrile in 190 mL of 2-ethoxyethanol was heated at reflux for four hours. The reaction mixture was cooled and was poured into 600 mL of water. The resulting aqueous slurry was stirred for a brief period and then filtered. The filter cake was washed with water and dried to yield 18.4 grams of 5-amino-1-(3-chloro-5-trifluoromethylpyridin-2-yl)-4-cyanopyrazole. The nmr spectrum was consistent with the proposed structure.

Step C
1-(3—Chloro-5-trifluoromethylpyridin-2-yl)-4-cyano-5-bis(methylcarbonyl)aminopyrazole Under a dry nitrogen atmosphere, a stirred mixture of 5.02 grams (0.0175 mole) of 5-amino-1-(3-chloro-5-trifluoromethylpyridin-2-yl)-4-cyanopyrazole and 12.7 grams (0.161 mole) of pyridine in 470 mL of methylene chloride was cooled to 5° C. Acetyl chloride (12.5 grams, 0.159 mole) was added dropwise. After the addition was complete, the reaction mixture was heated at reflux for approximately 20 hours. The mixture was then cooled, treated with decolorizing charcoal, and filtered through a pad of Celite ® filter aid. The filtrate was evaporated under reduced pressure, leaving a residue. This residue was stirred vigorously with a mixture of water and diethyl ether. The diethyl ether was allowed to evaporate at room temperature and pressure, leaving an aqueous slurry, which was cooled in an ice bath and then filtered. The filter cake was washed with water and air dried to yield 6.6 grams of 1(3-chloro-5-trifluoromethylpyridin-2-yl)-4-cyano-5-bis(methylcarbonyl)aminopyrazole, m.p. 129.5°–132° C. The nmr spectrum was consistent with the proposed structure.

Step D
1-(3-Chloro-5-trifluoromethylpyridin-2-yl)-4-cyano-5-methylcarbonylaminopyrazole A stirred mixture of 0.32 gram ($8.6 \times 10^{-4}$ mole) of 1-(3-chloro-5-trifluoromethylpyridin-2-yl)-4-cyano-5-bis- (methylcarbonyl)aminopyrazole, 10 mL of water, and 10 mL of ethanol was heated at reflux for four hours. The mixture was cooled, and most of the ethanol was removed by distillation under reduced pressure. The aqueous pot residue, which contained a solid, was diluted with water, and the mixture was filtered. The filter cake was dried to yield 0.22 gram of 1-(3-chloro-5-trifluoromethylpyridin-2-yl)-4-cyano-5-methylcarbonylaminopyrazole. The nmr spectrum was consistent with the proposed structure.

Step E
1-(3—Chloro-5-trifluoromethylpyridin-2-yl)-4-cyano-(N-methylcarbonyl-N-methylcarbonyloxymethylcarbonyl)aminopyrazole A stirred solution of 0.22 gram ($6.7 \times 10^{-4}$ mole) of 1-(3-chloro-5-trifluoromethylpyridin-2-yl)-4-cyano-5-methylcarbonylaminopyrazole and 0.081 gram ($8.0 \times 10^{-4}$ mole) of triethylamine in 25 mL of tetrahydrofuran was cooled to −5° C. Acetoxyacetyl chloride (0.10 gram, $7.3 \times 10^{-4}$ mole) was added, and the mixture was allowed to warm to room temperature. The reaction mixture was heated at reflux for 30 minutes and then cooled to 0° C. Additional acetoxyacetyl chloride (0.05 gram) and triethylamine (0.04 gram) were added, and the mixture was heated at reflux for 30 minutes. The mixture was cooled and filtered. The filtrate was evaporated under reduced pressure, leaving a residue, which was diluted with water and stirred, forming a waxy solid. This solid was recrystallized from ethanol and water to yield 0.15 gram of 1-(3-chloro-5-trifluoromethylpyridin-2-yl)-4-cyano-5-(N-methylcarbonyl-N-methylcarbonyloxymethylcarbonyl)aminopyrazole, m.p. 170°-173° C. (Compound 26 of Table 1). The nmr spectrum was consistent with the proposed structure.

EXAMPLE 4

Method D 1-(3-Chloro-5-Trifluoromethyl-6-Phenylmethylaminopyridin-2-yl)-4-Cyano-5-Ethylcarbonylaminopyrazole (Compound 53)

Step A
3,6-Dichloro-5-trifluoromethylpyridin-2-ylhydrazine

To a stirred mixture of 127.0 grams (0.507 mole) of 2,3,6-trichloro-5-trifluoromethylpyridine and 62.0 grams (0.632 mole) of potassium acetate in 470 mL of ethanol was added dropwise 17.9 grams (0.557 mole) of anhydrous hydrazine. During the addition the reaction temperature rose to 55° C., and a yellow slurry formed. This mixture was stirred at room temperature for approximately sixteen hours and then diluted with two liters of diethyl ether and shaken. The resultant mixture was filtered, and the filtrate was evaporated under reduced pressure, leaving a solid residue. This solid was purified by crystallization from 445 mL of methanol and 235 mL of water to yield, after drying, 91.5 grams of 3,6-dichloro-5-trifluoromethylpyridin-2-ylhydrazine. The nmr spectrum was consistent with the proposed structure.

Step B
3,6-Dichloro-5-trifluoromethylpyridin-2-ylhydrazomethylenemalononitrile To a stirred mixture of 30.0 grams (0.246 mole) of ethoxymethylenemalononitrile in 186 mL of water and 370 mL of glacial acetic acid was added 60.0 grams (0.244 mole) of 3,6-dichloro-5-trifluoromethylpyridin-2-ylhydrazine. After stirring for four hours at room temperature this mixture was a clear, wine-red solution, which was stirred for an additional 20 hours. A small sample of the reaction solution, on dilution with water, formed an oily resin, from which the supernatant liquid was decanted. When the resin was stirred with a small portion of chloroform, a granular, yellow solid formed. When this solid was added to the reaction solution, a precipitate formed. This mixture was stirred for 30 minutes and then poured into 1600 mL of water. This aqueous mixture was stirred occasionally with a glass rod during a one hour period. The aqueous mixture was filtered, the filter cake washed with water and air-dried to yield 45.1 grams of 3,6-dichloro-5-trifluoromethylpyridin-2-ylhydrazomethylenemalononitrile, m.p. 144°-147° C. The nmr spectrum was consistent with the proposed structure.

Step C
5-Amino-1-(3,6-dichloro-5-trifluoromethylpyridin-2-yl)-4-cyanopyrazole A stirred solution of 45.1 grams (0.140 mole) of 3,6-dichloro-5-trifluoromethylpyridin-2-ylhydrazomethylenemalononitrile in 300 mL of 2-ethoxyethanol was heated at reflux for approximately 1.5 hours. The solvent was removed by distillation under reduced pressure, leaving a slurry-like residue. This residue was washed twice with 300 to 400 mL portions of n-pentane. The resultant solid was dried to yield 38.6 grams of 5-amino-1-(3,6-dichloro-5-trifluoromethylpyridin-2-yl)-4-cyanopyrazole. The nmr spectrum was consistent with the proposed structure.

Step D
5-Amino-1-(3-chloro-5-trifluoromethyl-6-phenylmethylaminopyridin-2-yl)-4-cyanopyrazole A stirred solution of 6.0 grams (0.019 mole) of 5-amino-1-(3,6-dichloro-5-trifluoromethylpyridin-2-yl)-4-cyanopyrazole and 15.4 grams (0.144 mole) of benzylamine in 100 mL of tetrahydrofuran was heated at reflux for 3.5 hours. The reaction mixture was cooled and filtered. The filtrate was evaporated under reduced pressure, leaving a residue. This residue was dissolved in methylene chloride, and the organic solution was washed in succession with water, dilute hydrochloric acid, and water. The washed organic phase was dried over anhydrous magnesium sulfate and filtered. The filtrate was evaporated under reduced pressure, leaving a pale yellow solid residue. This residue, in 200 mL of petroleum ether, was heated to reflux and then allowed to cool to room temperature. The mixture was filtered, and the filter cake was dried to yield 3.0 grams of 5-amino-1-(3-chloro-5-trifluoromethyl-6-phenylmethylaminopyridin-2-yl)-4-cyanopyrazole. The nmr spectrum was consistent with the proposed structure.

Step E
1-(3-Chloro-5-trifluoromethyl-6-phenylmethylaminopyridin-2-yl)-4-cyano-5-ethylcarbonylaminopyrazole A stirred solution of 0.5 gram (0.001 mole) of 5-amino-1-(3-chloro-5-trifluoromethyl-6-phenylmethylaminopyridin-2-yl)-4-cyanopyrazole and 1.0 gram (0.013 mole) of pyridine in 25 mL of methylene chloride was cooled to −10° C. A solution of 1.2 grams (0.013 mole) of propionyl chloride in 10 mL of methylene chloride was added dropwise. After completion of the addition, the reaction mixture was allowed to warm to room temperature and then was heated at reflux for approximately 19 hours. The reaction mixture was cooled and evaporated under reduced pressure, leaving an oil. This oil was partitioned between diethyl ether and water. The organic phase was washed in succession with water, dilute hydrochloric acid, and water. The washed organic phase was evaporated under reduced pressure, leaving a residue. This residue was dissolved in 13 mL of ethanol and 13 mL of water. The resultant mixture was stirred and heated at reflux. Potassium carbonate (0.20 gram, 0.0014 mole) was added, and the mixture was stirred and heated at reflux for approximately 15 minutes. The solvents were removed by distillation under reduced pressure, leaving a waxy solid. This solid was purified by crystallization from ethanol and water to yield 0.51 gram of 1-(3-chloro-5-trifluoromethyl-6-phenylmethylaminopyridin-2-yl)-4-cyano-5-ethylcarbonylaminopyrazole, m.p. 139°-142° C. (Compound 53 of Table 1). The nmr spectrum was consistent with the proposed structure.

EXAMPLE 5

Method E

4-Chloro-1-(2,3,5,6-Tetrafluoro-4-Trifluoromethylphenyl)-5-(N-Methylcarbonyl-N-Methylcarbonyloxymethylcarbonyl)Aminopyrazole (Compound 1)

Step A
4-Chloro-1-(2,3,5,6-tetrafluoro-4-trifluoromethylphenyl)-5-methylcarbonylaminopyrazole A solution of 0.80 gram (0.0023 mole) of 1-(2,3,5,6-tetrafluoro-4-trifluoromethylphenyl)-5-methylcarbonylaminopyrazole (Step C of Example 1) in 25 mL of methylene chloride was cooled to $-5°$ C. Sulfuryl chloride (9.35 gram, 0.0026 mole) was added dropwise during a two minute period. After the addition was complete, the reaction mixture was allowed to warm to room temperature and was stirred for 1.5 hours. The reaction mixture was diluted with methylene chloride and washed in succession with an aqueous, saturated sodium bicarbonate solution and water. The organic phase was evaporated under reduced pressure to yield 0.82 gram of 4-chloro-1-(2,3,5,6-tetrafluoro-4-trifluoromethylphenyl)-5-methylcarbonylaminopyrazole as a white solid, m.p. 45°–47° C. The nmr spectrum was consistent with the proposed structure.

Step B
4-Chloro-1-(2,3,5,6-tetrafluoro-4-trifluoromethylphenyl)-5-(N-methylcarbonyl-N-methylcarbonyloxymethylcarbonyl)aminopyrazole A stirred solution of 0.30 gram (0.0013 mole) of 4-chloro-1-(2,3,5,6-tetrafluoro-4-trifluoromethylphenyl)-5-methylcarbonylaminopyrazole and 0.6 mL of triethylamine in 15 mL of tetrahydrofuran was cooled to $-5°$ C. Acetoxyacetyl chloride (0.55 gram, 0.0040 mole) was added, and the mixture was allowed to warm to room temperature. The reaction mixture was filtered, and the filtrate was evaporated under reduced pressure, leaving a residue. This residue was dissolved in methylene chloride and washed with water. The organic phase was dried over anhydrous magnesium sulfate and filtered. The filtrate was evaporated under reduced pressure, leaving a gummy solid. This solid was stirred in a small portion of ethanol to yield a white solid. This mixture was filtered, and the filter cake was dried to yield 0.29 gram of 4-chloro-1-(2,3,5,6-tetrafluoro-4-trifluoramethylphenyl)-5-(N-methylcarbonyl-N-methylcarbonyloxymethylcarbonyl)aminopyrazole (Compound 1 of Table 1). The nmr spectrum was consistent with the proposed structure.

Representative compounds of the invention prepared by the methods exemplified above are shown in Table 1. Characterizing properties of these compounds are given in Table 2.

HERBICIDAL ACTIVITY

The 1-(substituted-aryl)-5-substituted-carbonylamino-4-substituted-pyrazoles of this invention were tested in pre- and postemergence evaluations using a variety of broadleaf and grasseous crops and weeds. The test species used in demonstrating the herbicidal activity of this invention include cotton (*Gossypium hirsutum* var. DPL61), soybean (*Glycine max* var. Williams), field corn (*Zea mays* var. Agway 425X), rice (*Oryza sativa* var. Labelle), wheat (*Triticum aestivum* var. Wheaton), morningglory (*Ipomea lacunosa* or *Ipomea hederacea*), wild mustard (*Brassica kaber*), velvetleaf (*Abutilon theophrasti*), barnyardgrass (*Echinochloa crusgalli*), green foxtail (*Setaria viridis*), johnsongrass (*Sorghum halepense*), blackgrass (*Alopecurus myosuroides*), common chickweed (*Stellaria media*), and common cocklebur (*Xanthium pennsylvanicum*).

Preparation of Flats

Preemergence

Two disposable fiber flats (8 cm × 15 cm × 25 cm) for each rate of application for each candidate herbicide are filled to an approximate depth of 6.5 cm with steam-sterilized sandy loam soil. The soil is leveled and impressed with a template to provide five or six evenly spaced furrows 13 cm long and 0.5 cm deep in each flat.

In one case, seeds of cotton, soybean, corn, rice, and wheat are planted in the furrows of the first flat, and seeds of morningglory, wild mustard, velvetleaf, barnyardgrass, green foxtail, and johnsongrass are planted in the furrows of the second flat. The six-row template is employed to firmly press the seeds into place. A topping soil of equal portions of sand and sandy loam soil is placed uniformly on top of each flat to a depth of approximately 0.5 em.

In another case, seeds of soybean, wheat, corn, green foxtail, and johnsongrass are planted in the furrows of the first flat, and seeds of velvetleaf, morningglory, common chickweed, cocklebur, and blackgrass are planted in the furrows of the second flat. The five-row template is employed to firmly press the seeds into place. A topping soil of equal portions of sand and sandy loam soil is placed uniformly on top of each flat to a depth of approximately 0.5 am.

In each case, the flats are first watered, then sprayed with a solution of test compound as described below.

Postemergence

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g for the four flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mi/flat). The remaining 30 ML portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 q candidate herbicide is divided into two 30 mL portions each containing 0.06 g of candidate herbicide. One of the 30 mL (0.06 q active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science society; Auburn University, Auburn, Ala., 1977. The rating system is as follows:

Herbicide Rating System

| Rating Percent Control | Description of Main Categories | Crop Description | Weed Description |
|---|---|---|---|
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfanated aliphatic polyester as wetting agents. Frequently additional wetting agent and/or oil will be added to the tank mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g., four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)1,3,5-triazine-2,4-diamine (atrazine), and 2-[4-chloro-6-(ethylamino)-1,3,5-triazin-2-yl]amino-2-methylpropanenitrite (cyanazine); dinitroaniline herbicides such as 2,6-dinitro-N,N-dipropyl-4-(trifluoromethyl)benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

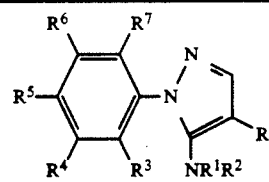

| Compound | R | R$^1$ | R$^2$ | R$^3$ | R$^4$ | R$^5$ | R$^6$ | R$^7$ |
|---|---|---|---|---|---|---|---|---|
| 1 | Cl | C(O)CH$_2$OC(O)CH$_3$ | C(O)CH$_3$ | F | F | CF$_3$ | F | F |
| 2 | CN | C(O)CH$_2$OC(O)CH$_3$ | C(O)CH$_2$OC(O)CH$_3$ | H | H | CF$_3$ | H | H |
| 3 | CN | C(O)CH$_2$OC(O)CH$_3$ | H | H | H | CF$_3$ | H | H |
| 4 | CN | C(O)CH$_2$OC(O)CH$_3$ | C(O)C$_2$H$_5$ | Cl | Cl | Cl | H | H |
| 5 | CN | C(O)CH$_2$OC(O)CH$_3$ | H | F | F | CF$_3$ | F | F |
| 6 | NO$_2$ | C(O)CH$_2$OH | H | Cl | H | CF$_3$ | H | H |
| 7 | NO$_2$ | C(O)CH$_2$OC(O)CH$_3$ | H | Cl | H | CF$_3$ | H | H |
| 8 | NO$_2$ | C(O)CH$_2$OH | H | Cl | H | CF$_3$ | H | Cl |
| 9 | NO$_2$ | C(O)CH$_2$OC(O)CH$_3$ | H | Cl | H | CF$_3$ | H | Cl |
| 10 | NO$_2$ | C(O)CH$_2$OSO$_2$NHCH$_3$ | H | Cl | H | CF$_3$ | H | Cl |
| 11 | NO$_2$ | C(O)CH$_2$OSO$_2$NHCH(CH$_3$)$_2$ | H | Cl | H | CF$_3$ | H | Cl |
| 12 | NO$_2$ | C(O)CH$_2$OH | H | F | F | CF$_3$ | F | F |
| 13 | NO$_2$ | C(O)CH$_2$OCH$_2$C$_6$H$_5$ | H | F | F | CF$_3$ | F | F |
| 14 | NO$_2$ | C(O)CH$_2$OC(O)CH$_3$ | H | F | F | CF$_3$ | F | F |
| 15 | NO$_2$ | C(O)C(CH$_3$)$_2$OC(O)CH$_3$ | H | F | F | CF$_3$ | F | F |
| 16 | NO$_2$ | C(O)CH$_2$OC(O)C$_6$H$_5$ | H | F | F | CF$_3$ | F | F |
| 17 | NO$_2$ | C(O)CH$_2$OC(O)CH$_3$ | C(O)CH$_2$OC(O)CH$_3$ | F | F | CF$_3$ | F | F |

TABLE 1-continued

| | | | | | | | | |
|---|---|---|---|---|---|---|---|---|
| 18 | $NO_2$ | $C(O)CH_2OCH_2C_6H_5$ | $C(O)CH_2OCH_2C_6H_5$ | F | F | $CF_3$ | F | F |
| 19 | $NO_2$ | $C(O)CH_2OC(O)CH_3$ | $C(O)CH_3$ | F | F | $CF_3$ | F | F |
| 20 | $NO_2$ | $C(O)CH_2OC(O)CH_3$ | $C(O)OCH_3$ | F | F | $CF_3$ | F | F |
| 21 | $NO_2$ | $C(O)CH_2OSO_2NHCH_3$ | H | F | F | $CF_3$ | F | F |
| 22 | $NO_2$ | $C(O)CH_2OSO_2NHC_2H_5$ | H | F | F | $CF_3$ | F | F |
| 23 | $NO_2$ | $C(O)CH_2OSO_2NHCH(CH_3)C_2H_5$ | H | F | F | $CF_3$ | F | F |

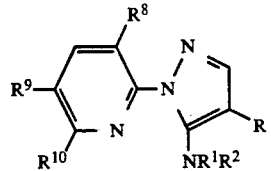

| Compound | R | $R^1$ | $R^2$ | $R^8$ | $R^9$ | $R^{10}$ |
|---|---|---|---|---|---|---|
| 24 | CN | $C(O)CH_2OC(O)CH_3$ | H | Cl | $CF_3$ | H |
| 25 | CN | $C(O)CH_2OC(O)CH_3$ | $CH_3$ | Cl | $CF_3$ | H |
| 26 | CN | $C(O)CH_2OC(O)CH_3$ | $C(O)CH_3$ | Cl | $CF_3$ | H |
| 27 | CN | $C(O)CH_2OC(O)CH_3$ | $C(O)CH_2OC(O)CH_3$ | Cl | $CF_3$ | H |
| 28 | CN | $C(O)CH_2OC(O)CH_3$ | H | Cl | $CF_3$ | Cl |
| 29 | CN | $C(O)CH_2OC(O)CH_3$ | $C(O)CH_3$ | Cl | $CF_3$ | Cl |
| 30 | CN | $C(O)CH_2OCH_3$ | H | Cl | $CF_3$ | $NHCH_2C_6H_5$ |
| 31 | $NO_2$ | $C(O)CH_2OH$ | H | Cl | $CF_3$ | H |
| 32 | $NO_2$ | $C(O)CH_2OC(O)CH_3$ | H | Cl | $CF_3$ | H |
| 33 | $NO_2$ | $C(O)CH_2OC(O)CH_3$ | $C(O)CH_3$ | Cl | $CF_3$ | H |
| 34 | $NO_2$ | $C(O)CH_2OC(O)CH_3$ | $C(O)CH_2OC(O)CH_3$ | Cl | $CF_3$ | H |
| 35 | $NO_2$ | $C(O)CH_2OC(O)CH_3$ | H | Cl | $CF_3$ | Cl |
| 36 | CN | $C(O)CH_3$ | H | Cl | $CF_3$ | $NHCH_3$ |
| 37 | CN | $C(O)CH_3$ | $C(O)CH_3$ | Cl | $CF_3$ | $NHCH_3$ |
| 38 | CN | $C(O)CH_3$ | H | Cl | $CF_3$ | $N(C_3H_7)_2$ |
| 39 | CN | $C(O)CH_3$ | H | Cl | $CF_3$ | $NHCH_2C{\equiv}CH$ |
| 40 | CN | $C(O)CH_3$ | H | Cl | $CF_3$ | $N(CH_3)CH_2C{\equiv}CH$ |
| 41 | CN | $C(O)C_2H_5$ | H | Cl | $CF_3$ | $N(CH_3)CH_2C{\equiv}CH$ |
| 42 | CN | $C(O)CH_3$ | $C(O)CH_3$ | Cl | $CF_3$ | $NHCH_2C{\equiv}CH$ |
| 43 | CN | $C(O)CH_3$ | $C(O)CH_3$ | Cl | $CF_3$ | $N(CH_3)CH_2C{\equiv}CH$ |
| 44 | CN | $C(O)CH_3$ | H | Cl | $CF_3$ | $NHCH_2C_6H_5$ |
| 45 | CN | $C(O)CH_3$ | $C(O)CH_3$ | Cl | $CF_3$ | $NHCH_2C_6H_5$ |
| 46 | CN | $C(O)CH_2Cl$ | H | Cl | $CF_3$ | $NHCH_2C_6H_5$ |
| 47 | CN | $C(O)CH_3$ | H | Cl | $CF_3$ | $NHCH(CH_3)C_6H_5$ |
| 48 | CN | $C(O)CH_3$ | $C(O)CH_3$ | Cl | $CF_3$ | $NHCH(CH_3)C_6H_5$ |
| 49 | CN | $C(O)CH_3$ | H | Cl | $CF_3$ | $NHCH_2C_6H_4\text{-}4\text{-}Cl$ |
| 50 | CN | $C(O)CH_3$ | $C(O)CH_3$ | Cl | $CF_3$ | $NHCH_2C_6H_4\text{-}4\text{-}Cl$ |
| 51 | CN | $C(O)CH_3$ | H | Cl | $CF_3$ | $NHCH_2C_6H_4\text{-}4\text{-}OCH_3$ |
| 52 | CN | $C(O)CH_3$ | $C(O)CH_3$ | Cl | $CF_3$ | $NHCH_2C_6H_4\text{-}4\text{-}OCH_3$ |
| 53 | CN | $C(O)C_2H_5$ | H | Cl | $CF_3$ | $NHCH_2C_6H_5$ |
| 54 | CN | $C(O)C_2H_5$ | H | Cl | $CF_3$ | $N(CH_3)CH_2C_6H_5$ |
| 55 | CN | $C(O)C_2H_5$ | $C(O)C_2H_5$ | Cl | $CF_3$ | $N(CH_3)CH_2C_6H_5$ |
| 56 | CN | $C(O)C_2H_5$ | H | Cl | $CF_3$ | $NHCH_2C_6H_4\text{-}4\text{-}Cl$ |
| 57 | CN | $C(O)C_2H_5$ | $C(O)C_2H_5$ | Cl | $CF_3$ | $NHCH_2C_6H_4\text{-}4\text{-}Cl$ |
| 58 | CN | $C(O)C_3H_7$ | H | Cl | $CF_3$ | $NHCH_2C_6H_5$ |
| 59 | CN | $C(O)C_3H_7$ | $C(O)C_3H_7$ | Cl | $CF_3$ | $NHCH_2C_6H_5$ |
| 60 | CN | $C(O)CH(CH_3)_2$ | H | Cl | $CF_3$ | $NHCH_2C_6H_5$ |
| 61 | CN | C(O)-cyclopropyl | H | Cl | $CF_3$ | $NHCH_2C_6H_5$ |
| 62 | CN | C(O)-cyclopropyl | C(O)-cyclopropyl | Cl | $CF_3$ | $NHCH_2C_6H_5$ |
| 63 | CN | $C(O)CH_3$ | H | Cl | $CF_3$ | NHCH$_2$-(tetrahydrofuran-2-yl) |
| 64 | CN | $C(O)CH_3$ | $C(O)CH_3$ | Cl | $CF_3$ | NHCH$_2$-(tetrahydrofuran-2-yl) |
| 65 | CN | $C(O)C_2H_5$ | H | Cl | $CF_3$ | NHCH$_2$-(tetrahydrofuran-2-yl) |
| 66 | CN | $C(O)C_2H_5$ | H | Cl | $CF_3$ | NHCH$_2$-(furan-2-yl) |

TABLE 1-continued

| | | | | | | |
|---|---|---|---|---|---|---|
| 67 | CN | C(O)C$_2$H$_5$ | H | Cl | CF$_3$ | NHCH$_2$-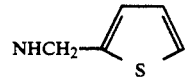 |
| 68 | CN | C(O)C$_2$H$_5$ | C(O)C$_2$H$_5$ | Cl | CF$_3$ | NHCH$_2$-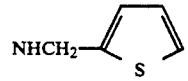 |

TABLE 2

Characterizing Properties

| Compound No. | M.P. (°C.) |
|---|---|
| 1 | 122–123 |
| 2 | 121–123 |
| 3 | 119–123 |
| 4 | 132–134 |
| 5 | 176–178 |
| 6 | 49–51 |
| 7 | oil |
| 8 | 157–160 |
| 9 | oil |
| 10 | solid |
| 11 | oil |
| 12 | solid |
| 13 | oil |
| 14 | waxy solid |
| 15 | oil |
| 16 | solid |
| 17 | 98–100 |
| 18 | oil |
| 19 | 159–160 |
| 20 | 141–142 |
| 21 | solid |
| 22 | 91–95 |
| 23 | solid |
| 24 | solid |
| 25 | solid |
| 26 | 170–173 |
| 27 | solid |
| 28 | solid |
| 29 | 167–170 |
| 30 | 149–151.5 |
| 31 | 67–70 |
| 32 | 119–121 |
| 33 | solid |
| 34 | solid |
| 35 | 148–151 |
| 36 | 181.5–183.5 |
| 37 | 153–156 |
| 38 | oil |
| 39 | 154–156 |
| 40 | 152–154 |
| 41 | solid |
| 42 | waxy solid |
| 43 | oil |
| 44 | 158–160 |
| 45 | 138–143 |
| 46 | waxy solid |
| 47 | solid |
| 48 | oil |
| 49 | 76 (dec) |
| 50 | 62 (dec) |
| 51 | solid |
| 52 | waxy solid |
| 53 | 139–142 |
| 54 | solid |
| 55 | 175–176.5 |
| 56 | oil |
| 57 | 126–128 |
| 58 | 128–131 |
| 59 | solid |
| 60 | solid |
| 61 | 166–167.5 |
| 62 | oil |
| 63 | solid |
| 64 | 154–156 |
| 65 | oil |
| 66 | oil |
| 67 | solid |
| 68 | oil |

TABLE 3

PREEMERGENCE HERBICIDAL ACTIVITY (% Control)

| Compound No. | 1 | 2 | 3 | 4 | 5 | 6 | 7 | 8 | 9 | 10 | 11 | 12 |
|---|---|---|---|---|---|---|---|---|---|---|---|---|
| Rate (kg/ha) | 0.5 | 2.0 | 0.5 | 0.5 | 0.5 | 0.5 | 0.5 | 0.5 | 0.5 | 0.5 | 0.25 | 0.5 |
| Species | | | | | | | | | | | | |
| Velvetleaf | 100 | 60 | 85 | 100 | 100 | 100 | 100 | 100 | 100 | 100 | 100 | 100 |
| Blackgrass | 80 | 50 | 50 | 100 | 80 | 85 | 85 | 95 | 95 | 100 | 85 | 95 |
| Soybean | 30 | 5 | 10 | 95 | 50 | 90 | 70 | 95 | 100 | 100 | 80 | 85 |
| Morningglory | 95 | 80 | 70 | 100 | 90 | 100 | 100 | 100 | 100 | 100 | 100 | 100 |
| Green foxtail | 95 | 30 | 70 | 100 | 100 | 100 | 100 | 100 | 100 | 100 | 100 | 100 |
| Johnsongrass | 85 | 50 | 70 | 100 | 90 | 100 | 100 | 100 | 100 | 100 | 100 | 95 |
| Chickweed | 10 | 10 | 15 | 100 | 70 | 100 | 100 | 100 | 100 | 100 | 95 | 95 |
| Wheat | 85 | 20 | 30 | 100 | 70 | 90 | 85 | 95 | 95 | 100 | 95 | 90 |
| Cocklebur | 90 | 50 | 50 | 95 | 95 | 90 | 85 | 100 | 95 | 100 | 85 | 100 |
| Corn | 95 | 60 | 80 | 95 | 100 | 100 | 100 | 100 | 95 | 100 | 100 | 95 |

| Compound No. | 13 | 14 | 15 | 16 | 17 | 18 | 19 | 20 | 21 | 22 | 23 | 24 |
|---|---|---|---|---|---|---|---|---|---|---|---|---|
| Rate (kg/ha) | 0.5 | 0.5 | 0.5 | 0.5 | 0.5 | 0.5 | 0.5 | 0.5 | 0.5 | 0.5 | 0.5 | 0.5 |
| Species | | | | | | | | | | | | |
| Velvetleaf | 100 | 100 | 100 | 100 | 100 | 100 | 100 | 100 | 100 | 100 | 100 | 95 |
| Blackgrass | 85 | 100 | 95 | 95 | 90 | 85 | 100 | 95 | 95 | 100 | 90 | 45 |
| Soybean | 80 | 70 | 70 | 85 | 40 | 40 | 85 | 40 | 90 | 85 | 30 | 85 |
| Morningglory | 95 | 100 | 100 | 100 | 100 | 100 | 100 | 100 | 100 | 100 | 100 | 100 |
| Green foxtail | 95 | 95 | 100 | 100 | 100 | 95 | 100 | 100 | 100 | 100 | 100 | 100 |
| Johnsongrass | 95 | 95 | 95 | 95 | 95 | 95 | 100 | 95 | 100 | 100 | 95 | 95 |
| Chickweed | 95 | 100 | 95 | 100 | 95 | 95 | 100 | 80 | 100 | 100 | 100 | 95 |
| Wheat | 80 | 95 | 85 | 95 | 70 | 80 | 90 | 85 | 95 | 95 | 90 | 70 |

TABLE 3-continued
PREEMERGENCE HERBICIDAL ACTIVITY (% Control)

| | | | | | | | | | | | | |
|---|---|---|---|---|---|---|---|---|---|---|---|---|
| Cocklebur | 100 | 100 | 95 | 100 | 100 | 100 | 100 | 100 | 100 | 100 | 85 | 95 |
| Corn | 95 | 95 | 95 | 95 | 95 | 95 | 95 | 95 | 95 | 95 | 95 | 100 |

| Compound No. | 25 | 26 | 27 | 28 |
|---|---|---|---|---|
| Rate (kg/ha) | 0.5 | 0.5 | 0.5 | 0.5 |
| Species | | | | |
| Velvetleaf | 80 | 100 | 100 | 100 |
| Blackgrass | 50 | 100 | 100 | 85 |
| Soybean | 40 | 100 | 95 | 25 |
| Morningglory | 95 | 100 | 100 | 55 |
| Green foxtail | 90 | 100 | 100 | 95 |
| Johnsongrass | 90 | 100 | 100 | 95 |
| Chickweed | 40 | 100 | 100 | 80 |
| Wheat | 80 | 100 | 100 | 35 |
| Cocklebur | 50 | 100 | 95 | 50 |
| Corn | 95 | 100 | 100 | 95 |

| Compound No. | 29 | 30 | 31 | 32 | 33 | 34 | 35 | 36 |
|---|---|---|---|---|---|---|---|---|
| Rate (kg/ha) | 0.5 | 1.0 | 0.5 | 0.5 | 0.5 | 0.5 | 0.5 | 2.0 |
| Species | | | | | | | | |
| Velvetleaf | 100 | 100 | 100 | 100 | 100 | 95 | 90 | 100 |
| Barnyardgrass | | 90 | | | | | | 100 |
| Blackgrass | 95 | | 100 | 100 | 100 | 40 | 70 | |
| Soybean | 15 | 30 | 100 | 100 | 100 | 55 | 0 | 100 |
| Morningglory | 95 | 100 | 100 | 100 | 100 | 100 | 85 | 100 |
| Green foxtail | 100 | 100 | 100 | 100 | 100 | 100 | 100 | 100 |
| Johnsongrass | 95 | 90 | 100 | 100 | 100 | 90 | 95 | 100 |
| Chickweed | 100 | | 100 | 100 | 100 | 95 | 90 | |
| Wheat | 70 | 90 | 100 | 100 | 100 | 95 | 50 | 100 |
| Cocklebur | 80 | | 95 | 95 | 95 | 95 | 0 | |
| Corn | 95 | 85 | 100 | 100 | 100 | 100 | 90 | 100 |
| Cotton | | 100 | | | | | | 100 |
| Rice | | 70 | | | | | | 100 |
| Wild mustard | | 100 | | | | | | 100 |

| Compound No. | 37 | 38 | 39 | 40 | 41 | 42 | 43 | 44 | 45 | 46 | 47 | 48 |
|---|---|---|---|---|---|---|---|---|---|---|---|---|
| Rate (kg/ha) | 2.0 | 1.0 | 1.0 | 1.0 | 1.0 | 1.0 | 1.0 | 2.0 | 2.0 | 1.0 | 1.0 | 1.0 |
| Species | | | | | | | | | | | | |
| Velvetleaf | 100 | 100 | 100 | 100 | 100 | 100 | 100 | 100 | 100 | 100 | 100 | 100 |
| Barnyardgrass | 100 | 95 | 100 | 100 | 100 | 100 | 95 | 100 | 100 | 95 | 100 | 95 |
| Soybean | 100 | 60 | 100 | 100 | 100 | 100 | 100 | 100 | 100 | 70 | 5 | 5 |
| Morningglory | 100 | 100 | 100 | 100 | 100 | 100 | 100 | 100 | 100 | 100 | 80 | 95 |
| Green foxtail | 100 | 100 | 100 | 100 | 100 | 100 | 100 | 100 | 100 | 100 | 100 | 100 |
| Johnsongrass | 100 | 100 | 100 | 100 | 100 | 100 | 100 | 100 | 100 | 100 | 100 | 100 |
| Wheat | 100 | 100 | 100 | 100 | 95 | 100 | 100 | 100 | 100 | 70 | 40 | 40 |
| Corn | 100 | 95 | 100 | 100 | 100 | 100 | 100 | 100 | 100 | 70 | 95 | 80 |
| Cotton | 100 | 90 | 100 | 100 | 95 | 100 | 100 | 100 | 100 | 90 | 70 | 60 |
| Rice | 95 | 95 | 100 | 95 | 100 | 100 | 95 | 100 | 95 | 60 | 70 | 70 |
| Wild mustard | 100 | 100 | 100 | 100 | 100 | 100 | 100 | 100 | 100 | 100 | 100 | 100 |

| Compound No. | 49 | 50 | 51 | 52 | 53 | 54 | 55 | 56 | 57 | 58 | 59 | 60 |
|---|---|---|---|---|---|---|---|---|---|---|---|---|
| Rate (kg/ha) | 1.0 | 1.0 | 1.0 | 1.0 | 1.0 | 1.0 | 1.0 | 1.0 | 1.0 | 1.0 | 1.0 | 1.0 |
| Species | | | | | | | | | | | | |
| Velvetleaf | 100 | 100 | 100 | 100 | 100 | 100 | 100 | 100 | 100 | 100 | 100 | 100 |
| Barnyardgrass | 85 | 100 | 100 | 90 | 95 | 95 | 100 | 100 | 10 | 100 | 95 | 100 |
| Soybean | 80 | 80 | 90 | 70 | 100 | 100 | 95 | 85 | 40 | 95 | 100 | 100 |
| Morningglory | 95 | 100 | 100 | 100 | 100 | 100 | 100 | 90 | 70 | 100 | 100 | 100 |
| Green foxtail | 100 | 100 | 100 | 100 | 100 | 100 | 100 | 90 | 100 | 100 | 100 | 100 |
| Johnsongrass | 95 | 100 | 100 | 70 | 95 | 95 | 100 | 100 | 30 | 100 | 100 | 100 |
| Wheat | 90 | 85 | 95 | 70 | 95 | 85 | 95 | 90 | 15 | 95 | 85 | 95 |
| Corn | 90 | 90 | 95 | 95 | 95 | 95 | 100 | 95 | 15 | 95 | 100 | 100 |
| Cotton | 95 | 90 | 95 | 90 | 100 | 100 | 95 | 95 | 50 | 95 | 85 | 90 |
| Rice | 95 | 95 | 95 | 95 | 95 | 95 | 95 | 95 | 20 | 85 | 80 | 95 |
| Wild mustard | 100 | 100 | 100 | 100 | 100 | 100 | 100 | 100 | 100 | 100 | 100 | 100 |

| Compound No. | 61 | 62 | 63 | 64 | 65 | 66 | 67 | 68 |
|---|---|---|---|---|---|---|---|---|
| Rate (kg/ha) | 1.0 | 1.0 | 1.0 | 1.0 | 0.5 | 1.0 | 1.0 | 1.0 |
| Species | | | | | | | | |
| Velvetleaf | 100 | 100 | 100 | 100 | 100 | 100 | 100 | 100 |
| Barnyardgrass | 100 | 100 | 100 | 100 | 100 | 100 | 100 | 100 |
| Soybean | 100 | 100 | 100 | 100 | 100 | 100 | 95 | 100 |
| Morningglory | 100 | 100 | 100 | 100 | 100 | 100 | 100 | 100 |
| Green foxtail | 100 | 100 | 100 | 100 | 100 | 100 | 100 | 100 |
| Johnsongrass | 100 | 100 | 100 | 100 | 100 | 100 | 100 | 100 |
| Wheat | 90 | 80 | 100 | 100 | 95 | 100 | 99 | 100 |
| Corn | 95 | 85 | 100 | 100 | 100 | 100 | 100 | 100 |
| Cotton | 85 | 90 | 90 | 100 | 100 | 100 | 100 | 100 |
| Rice | 95 | 95 | 100 | 100 | 95 | 100 | 100 | 100 |

TABLE 3-continued

| PREEMERGENCE HERBICIDAL ACTIVITY (% Control) | | | | | | | | |
|---|---|---|---|---|---|---|---|---|
| Wild mustard | 100 | 100 | 100 | 100 | 100 | 100 | 100 | 100 |

TABLE 4

POSTEMERGENCE HERBICIDAL ACTIVITY (% Control)

| Compound No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Rate (kg/ha) | 0.5 | 2.0 | 2.0 | 0.5 | 0.5 | 0.5 | 0.5 | 0.5 | 0.5 | 0.5 | 0.25 | 0.5 | 0.5 | 0.5 |
| Species | | | | | | | | | | | | | | |
| Velvetleaf | 90 | 40 | 60 | 100 | 100 | 70 | 80 | 95 | 100 | 100 | 95 | 100 | 95 | 100 |
| Blackgrass | 15 | 40 | 50 | 95 | 40 | 15 | 50 | 70 | 70 | 95 | 85 | 95 | 85 | 100 |
| Soybean | 70 | 50 | 40 | 95 | 70 | 95 | 95 | 95 | 95 | 100 | 95 | 80 | 95 | 90 |
| Morningglory | 85 | 60 | 50 | 100 | 100 | 80 | 95 | 95 | 100 | 90 | 95 | 100 | 100 | 100 |
| Green foxtail | 100 | 70 | 80 | 95 | 100 | 90 | 85 | 100 | 100 | 100 | 100 | 100 | 100 | 100 |
| Johnsongrass | 70 | 30 | 20 | 95 | 90 | 100 | 90 | 95 | 95 | 100 | 85 | 95 | 95 | 100 |
| Chickweed | 20 | 40 | 40 | 100 | 50 | 90 | 95 | 100 | 100 | 100 | 100 | 100 | 100 | 100 |
| Wheat | 20 | 40 | 40 | 95 | 70 | 70 | 30 | 50 | 60 | 95 | 80 | 70 | — | 90 |
| Cocklebur | 90 | 15 | 15 | 100 | 100 | 60 | 70 | 90 | 90 | 100 | 100 | 100 | 100 | 100 |
| Corn | 30 | 50 | 60 | 95 | 95 | 95 | 85 | 80 | 90 | 100 | 85 | 95 | 95 | 95 |

| Compound No. | 15 | 16 | 17 | 18 | 19 | 20 | 21 | 22 | 23 | 24 | 25 | 26 | 27 | 28 |
|---|---|---|---|---|---|---|---|---|---|---|---|---|---|---|
| Rate (kg/ha) | 0.5 | 0.5 | 0.5 | 0.5 | 0.5 | 0.5 | 0.5 | 0.5 | 0.5 | 0.5 | 0.5 | 0.5 | 0.5 | 0.5 |
| Species | | | | | | | | | | | | | | |
| Velvetleaf | 90 | 100 | 100 | 85 | 100 | 100 | 100 | 100 | 100 | 100 | 30 | 100 | 100 | 100 |
| Blackgrass | 85 | 85 | 90 | 80 | 95 | 85 | 100 | 100 | 80 | 10 | 15 | 95 | 100 | 20 |
| Soybean | 60 | 85 | 80 | 95 | 80 | 95 | 95 | 95 | 95 | 85 | 70 | 100 | 95 | 25 |
| Morningglory | 100 | 100 | 100 | 100 | 100 | 100 | 100 | 100 | 100 | 100 | 95 | 100 | 100 | 85 |
| Green foxtail | 95 | 100 | 100 | 100 | 100 | 100 | 100 | 100 | 100 | 95 | 20 | 100 | 100 | 95 |
| Johnsongrass | 90 | 95 | 95 | 95 | 100 | 100 | 100 | 100 | 100 | 60 | 40 | 95 | 100 | 90 |
| Chickweed | 90 | 90 | 100 | 100 | 95 | 90 | 100 | 100 | 100 | 95 | 10 | 100 | 100 | 95 |
| Wheat | 40 | — | 100 | — | 80 | 60 | 90 | 85 | 80 | 20 | 10 | 95 | 90 | 0 |
| Cocklebur | 90 | 100 | 100 | 95 | 100 | 100 | 100 | 100 | 95 | 95 | 40 | 100 | 95 | 40 |
| Corn | 80 | 95 | 100 | 95 | 95 | 85 | 95 | 100 | 95 | 40 | 60 | 95 | 85 | 35 |

| Compound No. | 29 | 30 | 31 | 32 | 33 | 34 | 35 | 36 |
|---|---|---|---|---|---|---|---|---|
| Rate (kg/ha) | 0.5 | 1.0 | 0.5 | 0.5 | 0.5 | 0.5 | 0.5 | 2.0 |
| Species | | | | | | | | |
| Velvetleaf | 100 | 100 | 100 | 100 | 100 | 90 | 80 | 100 |
| Barnyardgrass | | 90 | | | | | | 100 |
| Blackgrass | 90 | | 85 | 95 | 100 | 0 | 50 | |
| Soybean | 60 | 70 | 95 | 95 | 100 | 85 | 80 | 100 |
| Morningglory | 95 | 100 | 100 | 100 | 100 | 90 | 95 | 100 |
| Green foxtail | 100 | 100 | 100 | 100 | 100 | 95 | 100 | 100 |
| Johnsongrass | 100 | — | 100 | 100 | 100 | 45 | 100 | 100 |
| Chickweed | 100 | | 100 | 100 | 100 | 95 | 95 | |
| Wheat | 15 | 70 | 95 | 100 | 95 | 10 | 20 | 100 |
| Cocklebur | 70 | | 95 | 95 | 95 | 80 | 60 | |
| Corn | 90 | 60 | 95 | 100 | 95 | 10 | 70 | 100 |
| Cotton | | 85 | | | | | | 100 |
| Rice | | 30 | | | | | | 100 |
| Wild mustard | | 50 | | | | | | 100 |

| Compound No. | 37 | 38 | 39 | 40 | 41 | 42 | 43 | 44 | 45 | 46 | 47 | 48 | 49 | 50 |
|---|---|---|---|---|---|---|---|---|---|---|---|---|---|---|
| Rate (kg/ha) | 2.0 | 1.0 | 1.0 | 1.0 | 1.0 | 1.0 | 1.0 | 2.0 | 2.0 | 1.0 | 1.0 | 1.0 | 1.0 | 1.0 |
| Species | | | | | | | | | | | | | | |
| Velvetleaf | 100 | 100 | 100 | 100 | 100 | 100 | 100 | 100 | 100 | 100 | 95 | 90 | 100 | 100 |
| Barnyardgrass | 100 | 70 | 95 | 100 | 100 | 100 | 100 | 100 | 100 | 95 | 100 | 100 | 95 | 100 |
| Soybean | 100 | 90 | 100 | 95 | 95 | 100 | 95 | 100 | 100 | 40 | 70 | 60 | 85 | 100 |
| Morningglory | 100 | 95 | 100 | 100 | 100 | 100 | 100 | 100 | 100 | 100 | 95 | 80 | 100 | 100 |
| Green foxtail | 100 | 95 | 100 | 100 | 95 | 95 | 100 | 100 | 100 | 95 | 90 | 95 | 95 | 100 |
| Johnsongrass | 100 | 90 | — | 100 | 95 | — | 100 | 100 | 100 | — | 100 | 100 | 95 | 100 |
| Wheat | 100 | 85 | 100 | 100 | 100 | 95 | 100 | 100 | 100 | 50 | 70 | 50 | 90 | 95 |
| Corn | 100 | 90 | 100 | 100 | 100 | 90 | 100 | 100 | 100 | 70 | 70 | 70 | 100 | 95 |
| Cotton | 100 | 95 | 100 | 100 | 100 | 100 | 100 | 100 | 100 | 50 | 95 | 100 | 100 | 100 |
| Rice | 100 | 80 | 85 | 95 | 100 | 85 | 95 | 100 | 100 | 60 | 70 | 30 | 80 | 80 |
| Wild mustard | 100 | 70 | 95 | 100 | 95 | 95 | 100 | 95 | 100 | 80 | 80 | 95 | 95 | 95 |

| Compound No. | 51 | 52 | 53 | 54 | 55 | 56 | 57 | 58 | 59 | 60 | 61 | 62 | 63 | 64 |
|---|---|---|---|---|---|---|---|---|---|---|---|---|---|---|

TABLE 4-continued

| POSTEMERGENCE HERBICIDAL ACTIVITY (% Control) | | | | | | | | | | | | | | |
|---|---|---|---|---|---|---|---|---|---|---|---|---|---|---|
| Rate (kg/ha) | 1.0 | 1.0 | 1.0 | 1.0 | 1.0 | 1.0 | 1.0 | 1.0 | 1.0 | 1.0 | 1.0 | 1.0 | 1.0 | 1.0 |
| Species | | | | | | | | | | | | | | |
| Velvetleaf | 100 | 100 | 100 | 100 | 100 | 100 | 100 | 100 | 100 | 100 | 100 | 100 | 100 | 100 |
| Barnyardgrass | 95 | 100 | 100 | 70 | 90 | 70 | 10 | 95 | 50 | 100 | 95 | 95 | 100 | 100 |
| Soybean | 100 | 95 | 100 | 100 | 95 | 100 | 70 | 100 | 95 | 100 | 95 | 100 | 100 | 100 |
| Morningglory | 100 | 100 | 100 | 100 | 100 | 100 | 30 | 100 | 100 | 100 | 100 | 100 | 100 | 100 |
| Green foxtail | 100 | 100 | 100 | 70 | 100 | 100 | 30 | 100 | 100 | 100 | 100 | 100 | 100 | 100 |
| Johnsongrass | 100 | 100 | 100 | 50 | 100 | 100 | 20 | 100 | 100 | 100 | 100 | 100 | 100 | 100 |
| Wheat | 95 | 95 | 100 | 90 | 95 | 95 | 40 | 100 | 85 | 100 | 100 | 95 | 100 | 100 |
| Corn | 100 | 100 | 100 | 70 | 100 | 100 | 40 | 95 | 90 | 90 | 95 | 95 | 100 | 100 |
| Cotton | 100 | 100 | 100 | 100 | 100 | 100 | 100 | 100 | 100 | 100 | 100 | 100 | 95 | 95 |
| Rice | 80 | 90 | 100 | 70 | 100 | 95 | 15 | 85 | 90 | 80 | 95 | 95 | 100 | 100 |
| Wild mustard | 100 | 95 | 100 | 100 | 95 | 100 | 50 | 100 | 100 | 100 | 100 | 100 | 100 | 85 |

| Compound No. | 65 | 66 | 67 | 68 |
|---|---|---|---|---|
| Rate (kg/ha) | 1.0 | 0.5 | 1.0 | 1.0 |
| Species | | | | |
| Velvetleaf | 100 | 100 | 100 | 100 |
| Barnyardgrass | 100 | 100 | 95 | 95 |
| Soybean | 95 | 100 | 95 | 95 |
| Morningglory | 100 | 100 | 95 | 100 |
| Green foxtail | 100 | 100 | 100 | 100 |
| Johnsongrass | 100 | — | 95 | 100 |
| Wheat | 100 | 100 | 100 | 100 |
| Corn | 90 | 80 | 95 | 90 |
| Cotton | 100 | 90 | 100 | 100 |
| Rice | 90 | 85 | 95 | 90 |
| Wild mustard | 100 | 95 | 100 | 100 |

I claim:
1. A herbicidal compound of the formula:

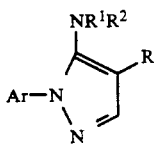

in which Ar is

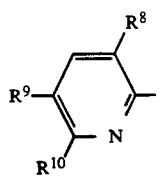

R is chlorine, cyano, or nitro;

$R^1$ is a group $-C(O)CR^{11}R^{12}-O-R^{13}$ in which $R^{11}$ and $R^{12}$ are independently hydrogen, or alyl, and $R^{13}$ is hydrogen, alkylcarbonyl, phenylcarbonyl, phenylmethyl, or alkylaminosulfonyl;

$R^2$ is hydrogen, alkyl, alkylcarbonyl, alkoxycarbonyl, or a group $-C(O)CR^{11}R^{12}-O-R^{13}$;

$R^8$ is halogen;

$R^9$ is haloalkyl;

$R^{10}$ is hydrogen, halogen, or a group $-NR^{14}R^{15}$ in which $R^{14}$ is hydrogen or alkyl; $R^{15}$ is alkyl, alkynyl, or a group $-CHR^{16}-Ar^1$ in which $R^{16}$ is hydrogen or alkyl; and $Ar^1$ is tetrahydrofuran-2-yl; furan-2-yl, thien-2-yl, phenyl, or phenyl substituted with halogen or alkoxy, and when $R^{10}$ is a group $-NR^{14}R^{15}$, in addition to the substituents listed above, $R^1$ may be alkylcarbonyl, haloalkylcarbonyl, or cycloalkylcarbonyl; and $R^2$ may be hydrogen, alkylcarbonyl, or cycloalkylcarbonyl;

wherein each alkyl and alkoxy contains 1 to 4 carbon atoms, each cycloalkyl contains 3-6 carbon atoms, and each alkynyl contains 3-4 carbon atoms with the proviso that when R is chlorine or nitro, $R^{13}$ is alkylcarbonyl, phenylcarbonyl, or alkylaminosulfonyl.

2. A compound of claim 1 in which R is cyano or nitro, and halogen is chlorine or fluorine.

3. A compound of claim 2 in which r is substituted pyridin-2-yl, R is cyano, $R^1$ is $-C(O)CR^{11}R^{12}-O-R^{13}$ or alkylcarbonyl, $R^{11}$ and $R^{12}$ are hydrogen, $R^{13}$ is alkylcarbonyl, $R^2$ is hydrogen or alkylcarbonyl, and $R^{10}$ is hydrogen.

4. A compound of claim 3 in which $R^{13}$ is acetyl, $R^2$ is hydrogen or acetyl, $R_8$ is chlorine, and $R_9$ is trifluoromethyl.

5. A compound of claim 4 in which $R^{13}$ and $R^2$ are acetyl.

6. An herbicidal composition comprising an herbicidally effective amount of a compound of claim 1 in admixture with a suitable carrier.

7. A method for controlling undesired plant growth which comprises applying to the locus where control is desired an herbicidally effective amount of the composition of claim 5.

* * * * *